US012616785B2

(12) United States Patent
Borillo et al.

(10) Patent No.: US 12,616,785 B2
(45) Date of Patent: May 5, 2026

(54) SORBENT REGENERATION CARTRIDGE FOR DIALYSIS

(71) Applicant: DIALITY INC., Irvine, CA (US)

(72) Inventors: Brandon Borillo, Irvine, CA (US); Tzu Tung Chen, Irvine, CA (US)

(73) Assignee: DIALITY INC., Irvine, CA (US)

( * ) Notice: Subject to any disclaimer, the term of this patent is extended or adjusted under 35 U.S.C. 154(b) by 1002 days.

(21) Appl. No.: 17/825,805

(22) Filed: May 26, 2022

(65) Prior Publication Data

US 2022/0378994 A1     Dec. 1, 2022

Related U.S. Application Data

(60) Provisional application No. 63/194,843, filed on May 28, 2021.

(51) Int. Cl.
A61M 1/16          (2006.01)
B01J 20/02          (2006.01)
B01J 20/28          (2006.01)

(52) U.S. Cl.
CPC ........ A61M 1/1696 (2013.01); B01J 20/0211 (2013.01); B01J 20/0292 (2013.01); B01J 20/28052 (2013.01); B01J 2220/62 (2013.01)

(58) Field of Classification Search
CPC .......................... A61M 1/1696; B01J 20/0211; B01J 20/0292; B01J 20/28052; B01J 2220/62
USPC ..................................................... 210/321.71
See application file for complete search history.

(56) References Cited

U.S. PATENT DOCUMENTS

| | | | |
|---|---|---|---|
| 3,669,878 A | 6/1972 | Marantz et al. | |
| 3,703,959 A | 11/1972 | Raymond | |
| 3,850,835 A | 11/1974 | Marantz et al. | |
| 4,071,444 A | 1/1978 | Ash et al. | |
| 4,256,718 A | 3/1981 | McArthur et al. | |
| 6,627,164 B1 | 9/2003 | Wong | |
| 6,818,196 B2 | 11/2004 | Wong | |
| 6,878,283 B2 | 4/2005 | Thompson | |
| 7,033,498 B2 | 4/2006 | Wong | |
| 7,241,272 B2 | 7/2007 | Karoor et al. | |
| 7,736,507 B2 | 6/2010 | Wong | |

(Continued)

FOREIGN PATENT DOCUMENTS

| | | |
|---|---|---|
| EP | 2 168 681 A2 | 3/2010 |
| JP | S63-59889 A | 3/1988 |

(Continued)

OTHER PUBLICATIONS

EP, 22812158.8 Extended Search Report, Feb. 11, 2025.
WO, PCT/US2022/031128 ISR and Written Opinion, Aug. 17, 2022.

*Primary Examiner* — Ekandra S. Miller-Cruz
(74) *Attorney, Agent, or Firm* — ONE LLP

(57)          ABSTRACT

Sorbent regeneration systems for use in dialysis machines are described. Sorbent regeneration cartridges may include a layer of urease, a layer of acid zirconium phosphate, and a layer of sodium zirconium phosphate. An apparatus for conducting dialysis may include a sorbent cartridge, and a dialyzer in fluid communication with the sorbent cartridge, wherein spent dialysate passes from the dialyzer to and through the sorbent cartridge, and wherein the sorbent cartridge comprises a layer of urease, a layer of acid zirconium phosphate, and a layer of sodium zirconium phosphate. The urease may be immobilized to or associated with a carrier.

14 Claims, 5 Drawing Sheets

250

(56) References Cited

U.S. PATENT DOCUMENTS

| | | | |
|---|---|---|---|
| 7,955,290 | B2 | 6/2011 | Karoor et al. |
| 8,002,726 | B2 | 8/2011 | Karoor et al. |
| 8,066,658 | B2 | 11/2011 | Karoor et al. |
| 8,409,444 | B2 | 4/2013 | Wong |
| 8,491,517 | B2 | 7/2013 | Karoor et al. |
| 8,640,887 | B2 | 2/2014 | Wong |
| 8,647,506 | B2 | 2/2014 | Wong |
| 8,672,145 | B2 | 3/2014 | Eisen |
| 8,758,626 | B2 | 6/2014 | Wong |
| 8,784,668 | B2 | 7/2014 | Beiriger |
| 9,144,640 | B2 | 9/2015 | Pudil et al. |
| 9,242,035 | B2 | 1/2016 | Karoor |
| 9,387,441 | B2 | 7/2016 | Ding et al. |
| 9,393,356 | B2 | 7/2016 | Karoor et al. |
| 9,517,296 | B2 | 12/2016 | Fulkerson et al. |
| 9,707,329 | B2 | 7/2017 | Merchant et al. |
| 9,707,332 | B2 | 7/2017 | Cho |
| 9,764,074 | B1 | 9/2017 | Childers et al. |
| 9,821,103 | B2 | 11/2017 | Sandford |
| 9,867,918 | B2 | 1/2018 | Merchant et al. |
| 10,004,839 | B2 | 6/2018 | Pudil et al. |
| 10,052,624 | B2 | 8/2018 | Menon et al. |
| 10,857,280 | B2 | 12/2020 | Wong et al. |
| 10,980,931 | B2 | 4/2021 | Karoor et al. |
| 2013/0180905 | A1 | 7/2013 | Wong |
| 2013/0213891 | A1 | 8/2013 | Karoor |
| 2014/0217028 | A1 | 8/2014 | Pudil et al. |
| 2015/0250937 | A1 | 9/2015 | Pudil et al. |
| 2015/0258266 | A1 | 9/2015 | Merchant et al. |
| 2015/0367051 | A1* | 12/2015 | Gerber ............... A61M 1/1696 210/209 |
| 2015/0367060 | A1 | 12/2015 | Gerber et al. |
| 2016/0151555 | A1 | 6/2016 | Bluchel et al. |
| 2016/0243541 | A1 | 8/2016 | Menon et al. |
| 2020/0040323 | A1 | 2/2020 | Yi et al. |
| 2020/0078507 | A1 | 3/2020 | Bluchel et al. |
| 2020/0164357 | A1 | 5/2020 | Ding et al. |
| 2021/0039016 | A1 | 2/2021 | Barrett et al. |
| 2021/0128807 | A1 | 5/2021 | Poppe et al. |

FOREIGN PATENT DOCUMENTS

| | | | |
|---|---|---|---|
| WO | WO 02/43859 | A2 | 6/2002 |
| WO | WO 02/044086 | A2 | 6/2002 |
| WO | WO 2013/019179 | A1 | 2/2013 |
| WO | WO 2020/113069 | A1 | 6/2020 |

* cited by examiner

Fluid
Flow

Zirconium Oxide — 212

Sodium Zirconium
Phosphate — 210

Hydrogen (Acid)
Zirconium Phosphate — 208

Activated Carbon — 206

Urease — 204

200

SORBENT REGENERATION CARTRIDGE FOR DIALYSIS

CROSS-REFERENCE TO RELATED APPLICATION

This application claims priority to, and the benefit of, U.S. Provisional Application No. 63/194,843, filed May 28, 2021, which is hereby expressly incorporated by reference in its entirety for all purposes.

BACKGROUND OF THE INVENTION

The present invention relates to cartridges that are useful in dialysis. In particular, the present invention relates in general to the regeneration or purification of used dialysate fluids. The present invention further relates to methods of conducting dialysis using certain cartridges and also relates to methods of making the cartridges.

More than 1 in 7 adults in the U.S. (approximately 15 of U.S. adults) are estimated to have chronic kidney (or renal) disease. In people who suffer from chronic kidney disease, their kidneys no longer clean their blood as well as healthy kidneys. Thus, toxic waste and extra fluid accumulates in the body. Dialysis is a treatment that removes the waste products and excess fluid that accumulate in the blood as a result of kidney failure. Chronic renal failure is when the renal function has deteriorated to about 25% of normal. This amount of deterioration causes significant changes in the blood chemistry and is about the time that people feel poorly enough that they seek medical care. If medical treatment is sought at that time, progression can be slowed. Late-stage chronic renal failure is when kidney function has decreased to 15%. End stage renal failure is when kidney function is at 5% of normal. Death will most likely result without treatment at this point.

Although there is no current cure for renal disease, there are several forms of treatment. One treatment is transplantation, which is where a human kidney is surgically placed in the body and connected to the bladder. After transplantation, daily medication is needed to keep the body from rejecting the transplanted kidney. Another treatment is peritoneal dialysis (PD). With this treatment, a mild saltwater solution containing dextrose and electrolytes called dialysate is put into the peritoneal cavity. Because there is a rich blood supply to this abdominal cavity, urea and other toxins from the blood and fluid are moved into the dialysate, thereby cleaning the blood. The dialysate is then drained from the peritoneum. Later "fresh" dialysate is again put into the peritoneum.

Another form of treatment is hemodialysis. This is a method of blood purification in which blood is continually removed from the body and passed through a dialyzer (artificial kidney) where metabolic waste and excess water are removed and pH and acid/base balance are normalized. The blood is simultaneously returned to the body. The dialyzer is a small disposable device consisting of a semipermeable membrane. The membrane allows the wastes, electrolytes, and water to cross but restricts the passage of large molecular weight proteins and blood cells. Blood is pumped across one side of the membrane as dialysate is pumped in the opposite direction across the other side of the membrane. The dialysate is highly purified water with salts and electrolytes added. The machine is a control unit that acts to pump and control pressures, temperatures, and electrolyte concentrations of the blood and the dialysate. The average length of one hemodialysis treatment is about 3.5 hours.

There are several types of hemodialysis—including single pass systems and sorbent systems. Single pass hemodialysis is the most common treatment for renal disease. These instruments are called single pass because the dialysate (cleaning solution) passes by the blood in the dialyzer one time and then is disposed. Single pass dialysis machines generally require: (1) a water source capable of delivering at least 1000-1500 ml/min (assuming a 50% rejection rate by the reverse osmosis(R.O.) system); (2) a water purification system sufficient of providing a continuous flow of 500-800 ml/min of purified water, (3) an electrical circuit of at least 15 amps in order to pump and heal 500-800 ml of water/min, and (4) a floor drain or any other receptacle capable of accommodating at least 500 ml of used dialysate/minute as well as the rejected water from the R.O. system.

Sorbent dialysis systems do not require a continuous water source, a separate water purification machine, or a floor drain because the system continuously regenerates a small volume of dialysate and incorporates a water treatment system within the machine. Therefore, sorbent systems are portable. The sorbent system can use 5-7 liters of sterile water, normal saline, half-normal saline, or dialysate from which dialysate is made or regenerated for an entire treatment. The sorbent system uses a sorbent cartridge, which removes uremic toxins without removing a majority of the salt allowing an efficient regeneration of used dialysate into fresh dialysate. The infusate system acts with the sorbent system to properly balance the electrolyte composition of the regenerated dialysate.

Several types of multi-layer sorbent cartridges have been used in dialysis machines that remove uremic toxins from patient's blood and reuse the dialysate solution via recirculation. These previous sorbent dialysis systems, however, did not efficiently remove uremic toxins without significant trade-off in sodium, pH control, treatment repeatability, total urea capacity, and sorbent cartridge size.

Accordingly, in the area of dialysis, it would be beneficial to create a sorbent cartridge system that has a higher capacity to remove uremic toxins and sodium within the cartridge.

SUMMARY

A sorbent cartridge is described that can be used to regenerate dialysate to be used in a dialysis system.

In many embodiments, a sorbent cartridge includes a layer of urease, a layer of acid zirconium phosphate, and a layer of zirconium phosphate. In some embodiments, in the layer of urease, the urease may be immobilized or associated with a carrier. In some embodiments, the urease may be conjugated to a carrier such as silica, diatoms (e.g., diatomaceous earth), alumina, activated carbon, metal hydroxides (based on iron, titanium, zirconium), metal phosphates (based on iron, titanium, zirconium, or cerium), high surface-area metal oxides (based on iron, titanium, zirconium, & cerium), anion or cation exchange polymers, or high surface area polymeric adsorbents.

In many embodiments, an apparatus for conducting dialysis comprising a sorbent cartridge, and a dialyzer in fluid communication with the sorbent cartridge, wherein spent dialysate passes from the dialyzer to and through the sorbent cartridge, and wherein the sorbent cartridge comprises a layer of immobilized urease, a layer of acid zirconium phosphate, and a layer of sodium form of zirconium phosphate.

DETAILED DESCRIPTION

In a dialysis treatment, a dialysis machine functions as an artificial kidney to remove uremic toxins, balance ionic molecules, and equilibrate pH for patients that lack healthy kidneys to perform those tasks. With the substitution of a multi-layer cartridge for a large volume of water, the cartridge is responsible for not only removing uremic toxins, but also balancing ionic salts and pH.

A hemodialysis system that incorporates a dialysate generator is described in US 2021/0128807, which is hereby expressly incorporated by reference in its entirety for all purposes. Various embodiments of a sorbent regeneration system, which includes a sorbent cartridge, described herein may be incorporated into the system described in US 2021/0128807 in place of the dialysate generator.

Figure 1A:
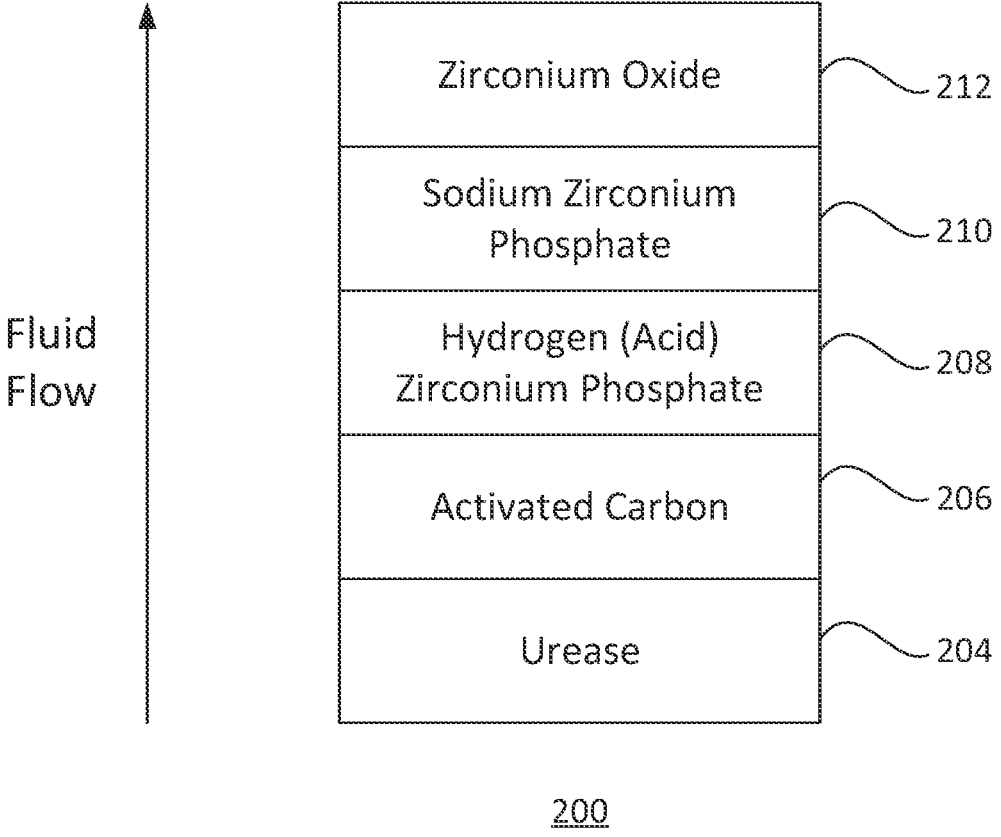
FIGS. 1A-1E are exemplary diagrams of sorbent cartridges according to various embodiments.

As seen in FIG. 1A, a cartridge 200 may include multiple layers of components to clean the dialysate. The cartridge 200 may include a layer of urease 204, activated carbon 206, acid zirconium phosphate 208, sodium zirconium phosphate 210, and zirconium hydroxide 212, or combinations thereof. Each layer may be separated by a filter, e.g., a filter paper. During regenerative dialysis, the used dialysate moves up through the layers of the cartridge 200. The urease 204 converts urea into ammonium carbonate. The activated carbon 206 absorbs organic metabolites such as creatine, uric acid, and nitrogenous metabolic waste of the patient as well as chlorine and chloramines from the water. The ammonia and ammonium ions are then removed by the hydrogen (acid) zirconium phosphate 208 and sodium zirconium phosphate 210 layers in exchange for $H^+$ and $Na^+$ ions. The urea hydrolysis then forms bicarbonate ($HCO_3^-$) and carbon dioxide ($CO_2$). The HZO adsorbs $HCO_3^-$, $PO_4^-$, and other anions, and releases hydroxide. The $CO_2$ gas bubbles are vented from the cartridge.

Although the layers of the cartridge are described in exemplary orders in FIGS. 1A-1E, it is to be understood that the layers may be arranged in any other possible order or permutation. For instance, the cartridge may be configured such that the activated carbon layer 206 contacts spent dialysate after either or both layers of zirconium phosphate 207, 208, 209, 210. The activated carbon layer 206 may be after the zirconium oxide 212 layer. The activated carbon layer 206 may also be before the urease layer 204.

The urease and carrier layer 204 serves the purpose of converting urea into ammonium (e.g., one molecule of urea to two molecules of ammonium), which is adsorbed by other layers of the cartridge. The layer 204 contains immobilized urease or free urease bound to sorbent carriers. When the urease is bound covalently, it keeps the urease active and stable for a lengthier period of time as compared to layers in which the urease is noncovalently associated with alumina. Moreover, alumina has been found to leach aluminum into the dialysis system, resulting in impermissibly high levels of aluminum. The urease may be covalently attached with glutaraldehyde to silica or diatoms coated with primary amines, thereby avoiding the inclusion of alumina in the sorbent cartridge. The primary amine coating may come from the treatment of silica or diatoms with APTES ((3-Aminopropyl) triethoxysilane) or APTMS (3-aminopropyltrimethoxysilane) or (3-Aminopropyl) silanetriol. Alternatively, urease can be bound by adsorption with materials that have a lower risk of toxic metal leaching such as titanium, cerium, iron, or zirconium oxides, hydroxides, or phosphates. The urease layer 204 may contain between about 100 g and about 400 g, alternatively between about 100 g and about 300 g, alternatively between about 150 g and about 250 g of urease, e.g., in the form of urease conjugated to silica.

In some embodiments, the urease layer 204 may include a mix of silica, diatoms, titanium oxide, iron oxide, iron phosphates, titanium phosphates, or cerium oxide. This mix may or may not be mixed with zirconium phosphate of various ratios of hydrogen to sodium.

In some embodiments, the urease layer 204 may contain urease in combination with one or more other components. As seen in cartridge 250 in FIG. 1D, the urease layer 204 may include urease and iron oxide. As seen in cartridge 260 in FIG. 1E, the urease layer 204 may include urease and a mix of sodium zirconium phosphate and hydrogen (acid) zirconium phosphate.

The activated carbon layer 206 may be located after or downstream of the urease and removes certain uremic toxins such as middle molecules, uric acid, oxidants and creatinine, as well as any toxins from the water/dialysate, such as heavy metals and organic molecules. In some embodiments, the activated carbon may be the final layer in the cartridge (see, e.g., FIGS. 1D and 1E). The activated carbon layer 206 may also capture unwanted enzymes and proteins that leached out from layer 204. Activated carbon can also be used as a filter medium to bind heavy metals, oxidants, and chloramines. The activated carbon layer 206 may contain between about 100 g and about 400 g, alternatively between about 100 g and about 300 g, alternatively between about 150 g and about 250 g of activated carbon. The particle size of the activated carbon may be between about 50 μm and about 600 μm, alternatively between about 75 μm and about 550 μm, alternatively between about 80 μm and about 550 μm, alternatively between about 75 μm and about 550 μm, alternatively between about 90 μm and about 550 μm, alternatively between about 90 μm and about 500 μm, alternatively between about 100 μm and about 500 μm. The activated carbon layer 206 may be located before or after any of the zirconium phosphate layers 208, 210 or the hydrous zirconium oxide layer 212.

Each of the hydrogen acid zirconium phosphate 208 and sodium zirconium phosphate 210 layers may be located after the activated carbon layer 206, or alternatively before the activated carbon layer 206 and the zirconium oxide layer. Zirconium phosphate in the sodium or hydrogen form may function as a cation exchanger and absorb cations such as ammonium ($NH_4^+$), calcium ($Ca^{+2}$), potassium ($K^+$), and magnesium ($Mg^{+2}$). In exchange for absorbing these cations, zirconium phosphate releases two other cations, sodium ($Na^+$) and hydrogen ($H^+$). Hydrous zirconium oxide acts as an anion exchanger. Thus, hydrous zirconium oxide can bind anions such as phosphate ($PO_4^-$) and fluoride ($F^-$) and hydroxide in exchange.

The hydrogen (acid) zirconium phosphate layer 208 may contain between about 200 g and about 1200 g, alternatively between about 200 g and about 800 g, alternatively between about 200 g and about 750 g, alternatively between about 300 g and about 700 g, alternatively between about 300 g and about 650 g, of hydrogen acid zirconium phosphate. The pH of the hydrogen (acid) zirconium phosphate in layer 208 may be between about 1 and about 4, alternatively between about 1 and about 3, alternatively between about 1 and about 2, alternatively between about 1.2 and about 1.8, alternatively between about 1.5 and about 1.8, alternatively about 1.0, alternatively about 1.1, alternatively about 1.2, alternatively about 1.3, alternatively about 1.4, alternatively about 1.5, alternatively about 1.6, alternatively about 1.7, alternatively about 1.8, alternatively about 1.9, alternatively about 2.0. The zirconium phosphate may be equilibrated at a particular pH with hydrogen to achieve the desired pH. The particle size of the hydrogen (acid) zirconium phosphate may be between about 20 μm and about 150 μm, alternatively between about 20 μm and about 130 μm, alternatively between about 30 μm and about 120 μm, alternatively between about 30 μm and about 110 μm, alternatively between about 40 μm and about 110 μm, alternatively between about 30 μm and about 100 μm, alternatively between about 40 μm and about 100 μm.

The sodium zirconium phosphate layer 210 may contain between about 200 g and about 1200 g, alternatively between about 200 g and about 800 g, alternatively between about 200 g and about 750 g, alternatively between about 300 g and about 700 g, alternatively between about 300 g and about 650 g, alternatively between about 400 g and about 650 g, alternatively between about 450 g and about 650 g of sodium zirconium phosphate. The pH of the sodium zirconium phosphate in layer 210 may be between about 2 and about 7, alternatively between about 3 and about 6.5, alternatively between about 3 and about 6.0, alternatively between about 3.5 and about 5.5, alternatively between about 4.5 and about 6.5, alternatively about 4.0, alternatively about 4.3, alternatively about 4.5, alternatively about 4.7, alternatively about 5.0, alternatively about 5.3, alternatively about 5.5, alternatively about 5.7, alternatively about 6.0, alternatively about 6.3, alternatively about 6.5, alternatively about 6.7. The particle size of the sodium zirconium phosphate may be between about 20 μm and about 150 μm, alternatively between about 20 μm and about 130 μm, alternatively between about 30 μm and about 120 μm, alternatively between about 30 μm and about 110 μm, alternatively between about 40 μm and about 110 μm, alternatively between about 30 μm and about 100 μm, alternatively between about 40 μm and about 100 μm.

The hydrogen (acid) zirconium phosphate layer 208 may bind ammonium molecules that were converted from the urea molecules while balancing out sodium ions by exchanging its hydrogen ions. With only a layer of hydrogen (acid) zirconium phosphate, the ammonium capacity is used faster than with sodium zirconium phosphate, but the acidic layer 208 removes an extra 10-35 millimoles/L of sodium from dialysate over the course of a treatment. The sodium zirconium phosphate layer 210 can bind ammonium molecules, with a greater capacity than hydrogen zirconium phosphate. The layer 208, 210 will adsorb a large quantity of sodium ions which will reduce its release of ammonium as more sodium is removed over time. This design maximizes the removal of ammonium by the zirconium phosphate while maximizing the amount of sodium removed. The excess sodium removed prevents excessive sodium from reentering the patient and allows the rebalance of a neutral pH in the dialysate solution.

Figure 1B:
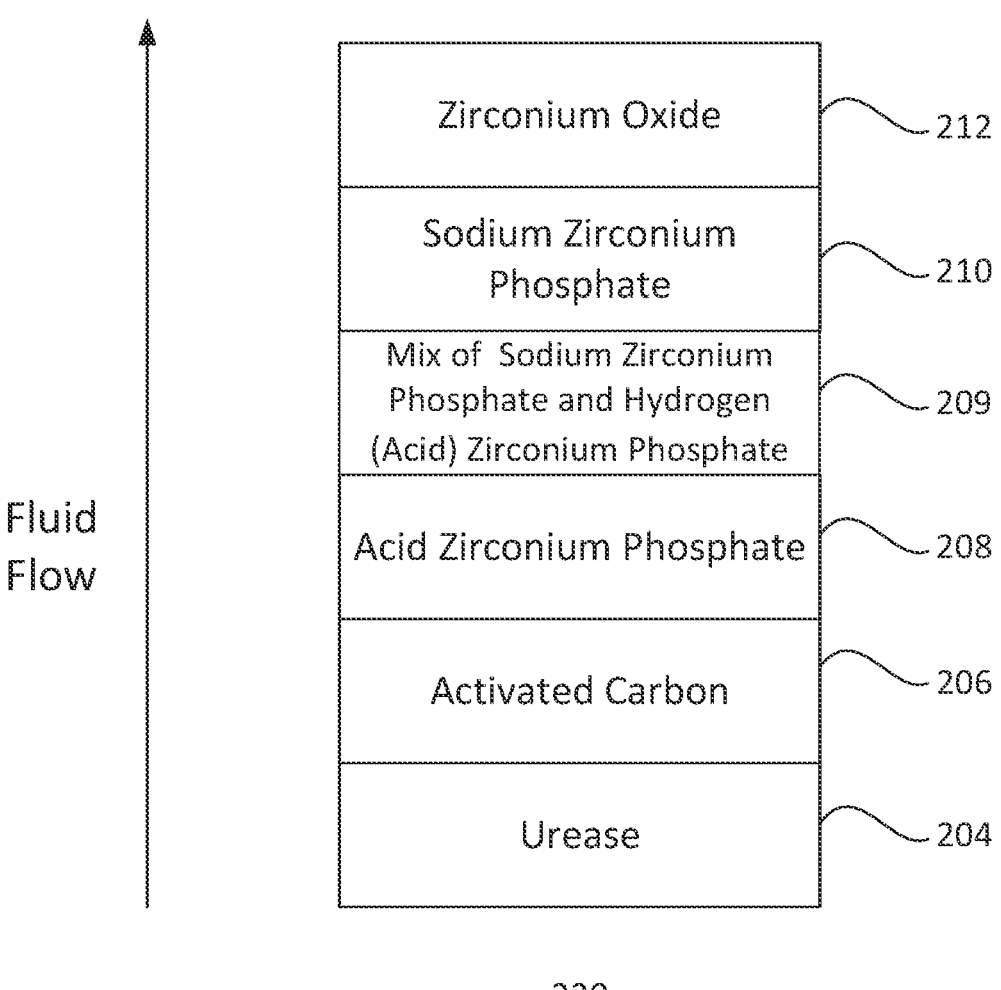

In some embodiments, the cartridge may contain more than two layers of zirconium phosphate. As seen in FIG. 1B, the cartridge 220 may contain a layer of hydrogen (acid) zirconium phosphate 208, partial acid/sodium zirconium phosphate 209, and sodium zirconium phosphate 210. The partial acid/sodium zirconium phosphate 209 may be a mixture of sodium and acid forms of zirconium phosphate. The partial acid/sodium zirconium phosphate 209 may be prepared by equilibrating zirconium phosphate in a salt/acid solution with some bound $H^+$ or $Na^+$, such that the properties of layer 209 may be similar to properties of homogenous mix layer 207. For example, acid zirconium phosphate may have a pH of approximately 1.5 if mixed into deionized (DI) water and sodium zirconium phosphate may have a pH of approximately 6-7 if mixed into DI water, but a varying among of $H^+/NA^+$ may be exchanged to get zirconium phosphate that may have a pH of about 5 in DI water.

Figure 1C:
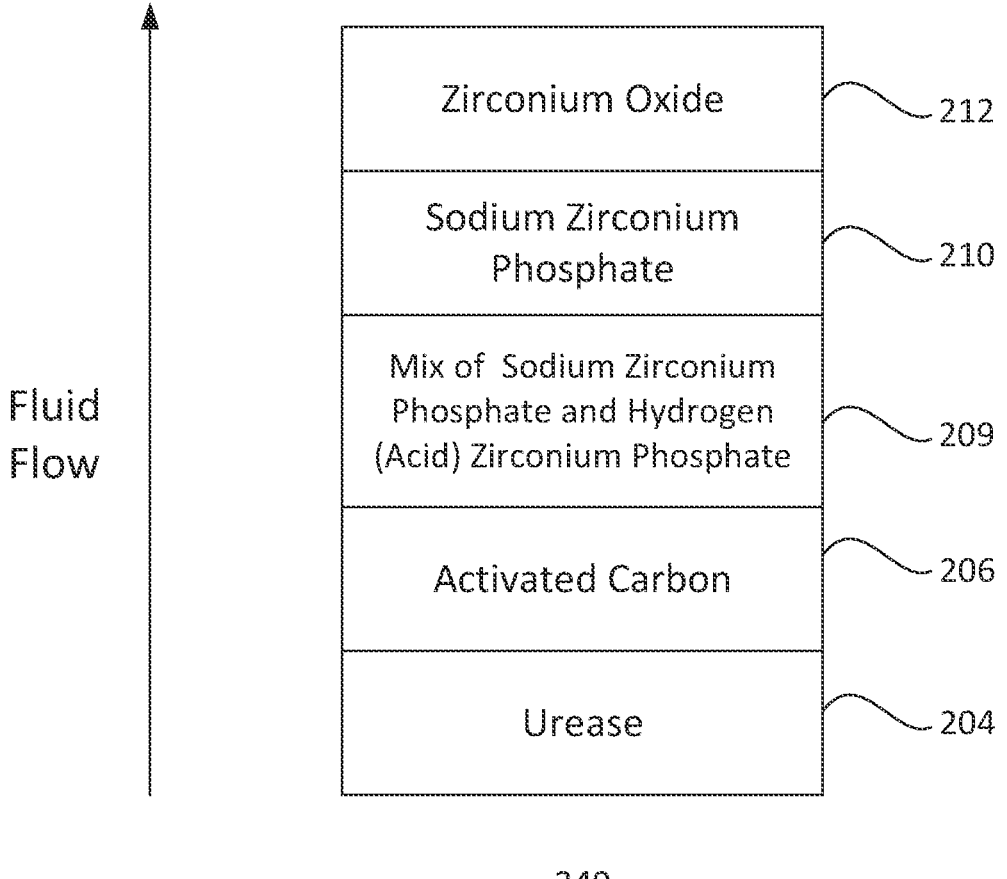
Figure 1D:
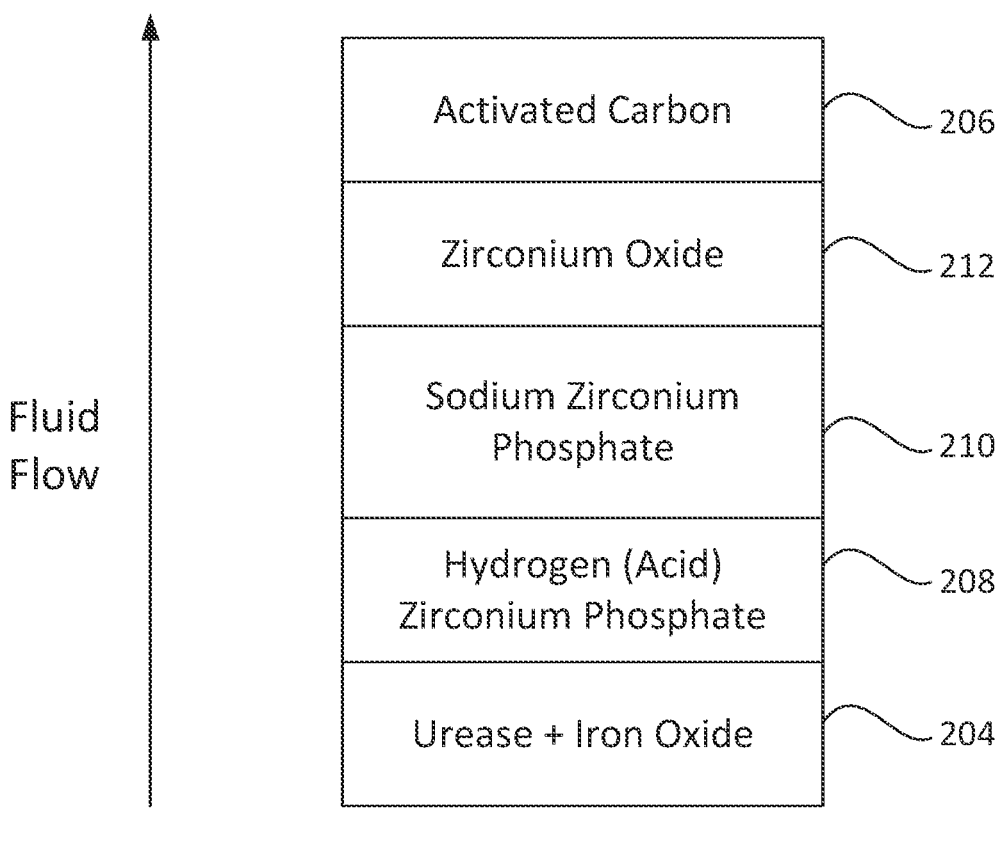
Figure 1E:
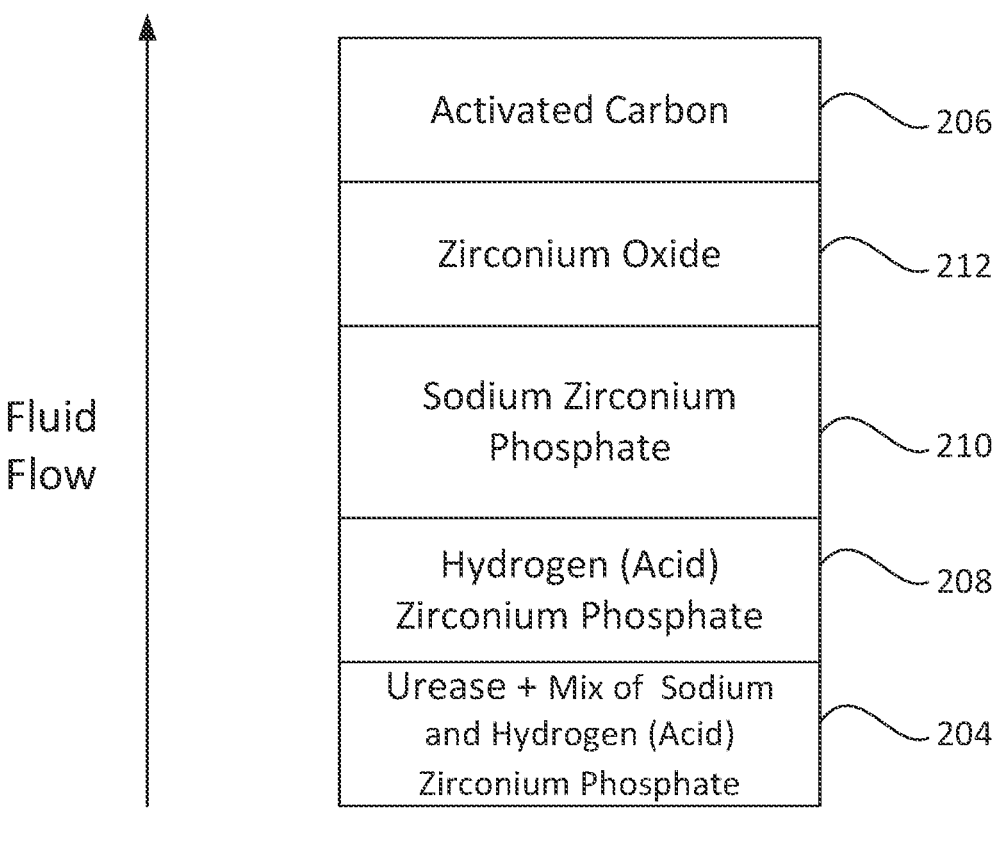

In other embodiments, as seen in FIG. 1C, the cartridge 240 may contain a layer of sodium zirconium phosphate and hydrogen (acid) zirconium phosphate 207 mixed together, e.g., a homogenous mixture, and a layer of sodium zirconium phosphate 210. The relative ratios of hydrogen (acid) zirconium phosphate:sodium zirconium phosphate in the mixed layer 207 may be between about 1:10 to about 3:1, alternatively about 0.2:3.0, alternatively about 0.2:2.5, alternatively about 0.2:2.0, alternatively about 0.25:2.0, alternatively about 0.3:2.0, alternatively about 0.4:2.0, alternatively about 0.5:2.0.

The multiple layers of acid zirconium phosphate 208 and partial hydrogen (acid)/sodium zirconium phosphate 209 (see FIG. 1B) or the mixed layer of sodium zirconium phosphate and hydrogen (acid) zirconium phosphate 207, followed by sodium zirconium phosphate 210 (see FIG. 1C) may provide higher ammonium capacity of between about 20-30% while balancing out sodium ions and readjusting dialysate pH. The additional and/or sequential layers may have a higher capacity of binding ammonium as compared to other sorbent cartridges that only have acid zirconium phosphate and sodium zirconium phosphate in their cartridges in mixtures to balance the pH of the system.

Excessive sodium zirconium phosphate in a cartridge can leach extra sodium ions into the dialysate, exchanging the sodium ions with the hydrogen in acid zirconium phosphate, which decreases the capacity of the cartridge and intensify the concentration of sodium above normal range. To balance sodium ions, the zirconium phosphate ratio may be focused on 50% or higher of acid zirconium phosphate. To counterbalance the drop of sodium concentration while keeping optimal cartridge configuration, sodium carbonate infusate may be controlled at various rates through a modified program.

The cartridge may also contain a layer of zirconium oxide or zirconium hydrous oxide or hydrous zirconium oxide or zirconium hydroxide 212, to eliminate phosphate ions from patient's body and the previous layers of the cartridge as well as any trace heavy metals that may have passed through the activated carbon layer. The layer 212 may be the last layer of the cartridge, or alternatively, may be located earlier in the fluid flow path.

The zirconium oxide layer 212 may contain between about 100 g and about 600 g, alternatively between about 100 g and about 500 g, alternatively between about 200 g and about 500 g, alternatively between about 200 g and about 450 g, alternatively between about 200 g and about 400 g of zirconium oxide or other transition metal oxide. In some embodiments, instead of zirconium oxide, layer 212 may contain titanium oxide, iron oxide, or some other transition metal oxide. Other embodiments may also be the hydrous form of transition metal oxides. The transition metal oxide may be equilibrated in a solution to an appropriate pH. The pH of the transition metal oxide, e.g., zirconium oxide, in layer 212 may be between about 2.0 and about 7.0, alternatively between about 3 and about 7.0, alternatively between about 3.5 and about 7.0, alternatively between about 5.0 and about 8.0, alternatively between about 4.0 and about 7.0, alternatively between about 4.5 and about 7.0, alternatively between about 4.5 and about 6.5, alternatively between about 5.5 and about 6.5, alternatively between about 6.0 and about 7.0, alternatively about 4.5, alternatively about 5.0, alternatively about 5.5, alternatively about 6.0, alternatively about 6.5, alternatively about 7.0, alternatively about 7.5, alternatively about 8.0, alternatively about 8.5. The particle size of the transition metal oxide may be between about 10 μm and about 150 μm, alternatively between about 10 μm and about 130 μm, alternatively between about 10 μm and about 120 μm, alternatively between about 20 μm and about 110 μm, alternatively between about 20 μm and about 105 μm, alternatively between about 20 μm and about 100 μm, alternatively between about 25 μm and about 100 μm.

Zirconium oxide may include many different forms, including but not limited to, zirconium oxide, zirconium hydroxide, zirconium oxide hydroxide, zirconium hydrous oxide, hydrous zirconium oxide, zirconium oxide with or without hydration, or combinations thereof.

The zirconium oxide layer 212 may be interchangeable with other metal oxides, such as iron oxide, titanium oxide, or cerium oxide. Iron oxide may include many different forms, including but not limited to, iron oxide, iron hydroxide, iron oxide hydroxide, iron hydrous oxide, and hydrous iron oxide. Titanium oxide may include many different forms, including but not limited to, titanium oxide, titanium hydroxide, titanium oxide hydroxide, titanium hydrous oxide, and hydrous titanium oxide. Cerium oxide may include many different forms, including but not limited to, cerium oxide, cerium hydroxide, Cerium oxide hydroxide, cerium hydrous oxide, and hydrous cerium oxide.

The possible chemicals that may leach out in the cartridge may include unwanted middle molecules—including proteins and enzymes, and phosphate from the zirconium phosphate sorbent layers. The activated carbon layer 206 of the cartridge is meant to bind unwanted middle in the dialysate. The zirconium oxide layer at the end of the cartridge may function to bind phosphate molecules that may leach out from the zirconium phosphate as the layers lose their capacity for ammonium.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible. The embodiments described herein are restated and expanded upon in the following paragraphs without explicit reference to the FIGURES.

In many embodiments, a sorbent cartridge includes a layer of urease, a layer of acid zirconium phosphate, and a layer of zirconium phosphate, wherein the urease is covalently immobilized or free urease bound or adsorbed to sorbent carriers.

In some embodiments, the cartridge is configured such that spent dialysate contacts the layer of urease before the spent dialysate contacts either the layer of acid zirconium phosphate or the layer of zirconium phosphate.

In some embodiments, the cartridge is configured such that spent dialysate contacts the layer of acid zirconium phosphate before the layer of zirconium phosphate.

In some embodiments, the cartridge further includes a layer of activated carbon. In some embodiments, the cartridge is configured such that spent dialysate contacts the layer of activated carbon after the spent dialysate contacts the layer of urease.

In some embodiments, the cartridge includes activated carbon as the last layer.

In some embodiments, the cartridge is configured with a layer of activated carbon as the final layer.

In some embodiments, the cartridge further includes a layer of zirconium oxide. In some embodiments, the zirconium oxide in the layer of zirconium oxide is zirconium oxide, zirconium hydroxide, zirconium oxide hydroxide, zirconium hydrous oxide, hydrous zirconium oxide, zirconium oxide with hydration, zirconium oxide without hydration, or combinations thereof. In some embodiments, the cartridge is configured such that spent dialysate contacts the layer of zirconium oxide after the spent dialysate contacts the layer of acid zirconium phosphate. In some embodiments, the cartridge is configured such that spent dialysate contacts the layer of zirconium oxide after the spent dialysate contacts the layer of zirconium phosphate.

In some embodiments, the layer of zirconium phosphate comprises sodium zirconium phosphate.

In some embodiments, urease in the layer of urease is immobilized.

In some embodiments, in the layer of urease, urease is covalently bound to silica.

In some embodiments, the layer of urease comprises a mixture of urease and a metal oxide. In some embodiments, the metal oxide is iron oxide. In some embodiments, the metal oxide is selected from the group consisting of iron oxide, iron hydroxide, iron oxide hydroxide, iron hydrous oxide, and hydrous iron oxide.

In some embodiments, the layer of urease comprises a mixture of urease and at least one zirconium phosphate.

In some embodiments, the layer of urease comprises a mixture of urease and at least two forms of zirconium phosphate. In some embodiments, the at least two forms of zirconium phosphate comprise sodium zirconium phosphate and acid zirconium phosphate.

In some embodiments, the cartridge further comprises an additional layer of zirconium phosphate. In some embodiments, the cartridge is configured such that spent dialysate contacts the additional layer of zirconium phosphate after the spent dialysate contacts the layer of activated carbon and before the spent dialysate contacts the layer of acid zirconium phosphate.

In some embodiments, the layer of acid zirconium phosphate further comprises zirconium phosphate to form a mixed layer of zirconium phosphate. In some embodiments, the mixed layer of zirconium phosphate comprises a ratio of acid zirconium phosphate:sodium zirconium phosphate of about 0.25:2.0.

In many embodiments, an apparatus for conducting dialysis comprising a sorbent cartridge, and a dialyzer in fluid communication with the sorbent cartridge, wherein spent dialysate passes from the dialyzer to and through the sorbent cartridge, and wherein the sorbent cartridge comprises a layer of urease and carrier, a layer of acid zirconium phosphate, and a layer of zirconium phosphate.

In some embodiments, the sorbent cartridge is configured such that the spent dialysate contacts the layer of urease before the spent dialysate contacts either the layer of acid zirconium phosphate or the layer of zirconium phosphate.

In some embodiments, the sorbent cartridge is configured such that the spent dialysate contacts the layer of acid zirconium phosphate before the layer of zirconium phosphate.

In some embodiments, the sorbent cartridge further includes a layer of activated carbon. In some embodiments, the layer of activated carbon is configured with a layer of activated carbon as the final layer. In some embodiments, the sorbent cartridge is configured such that the spent dialysate contacts the layer of activated carbon after the spent dialysate contacts the layer of urease.

In some embodiments, the sorbent cartridge further includes a layer of zirconium oxide. In some embodiments, the zirconium oxide in the layer of zirconium oxide is zirconium oxide, zirconium hydroxide, zirconium oxide hydroxide, zirconium hydrous oxide, hydrous zirconium oxide, zirconium oxide with hydration, zirconium oxide without hydration, or combinations thereof. In some embodiments, the sorbent cartridge is configured such that spent dialysate contacts the layer of zirconium oxide after the spent dialysate contacts the layer of acid zirconium phosphate. In some embodiments, the sorbent cartridge is configured such that spent dialysate contacts the layer of zirconium oxide after the spent dialysate contacts the layer of zirconium phosphate.

In some embodiments, the layer of zirconium phosphate comprises sodium zirconium phosphate.

In some embodiments, urease in the layer of urease is immobilized.

In some embodiments, in the layer of urease, urease is covalently bound to silica.

In some embodiments, the layer of urease comprises a mixture of urease and a metal oxide. In some embodiments, the metal oxide is iron oxide. In some embodiments, the metal oxide is selected from the group consisting of iron oxide, iron hydroxide, iron oxide hydroxide, iron hydrous oxide, and hydrous iron oxide.

In some embodiments, the layer of urease comprises a mixture of urease and at least one zirconium phosphate.

In some embodiments, the layer of urease comprises a mixture of urease and at least two forms of zirconium phosphate.

In some embodiments, the at least two forms of zirconium phosphate comprise sodium zirconium phosphate and acid zirconium phosphate.

In some embodiments, the cartridge further comprises an additional layer of zirconium phosphate. In some embodiments, the cartridge is configured such that spent dialysate contacts the additional layer of zirconium phosphate after the spent dialysate contacts the layer of activated carbon and before the spent dialysate contacts the layer of acid zirconium phosphate.

In some embodiments, the layer of acid zirconium phosphate further comprises zirconium phosphate to form a mixed layer of zirconium phosphate. In some embodiments, the mixed layer of zirconium phosphate comprises a ratio of acid zirconium phosphate:sodium zirconium phosphate of about 0.25:2.0.

What is claimed:

1. A sorbent cartridge comprising a layer of urease and iron hydroxide, a layer of acid zirconium phosphate, and a layer of zirconium phosphate, wherein the layer of acid zirconium phosphate is between the layer of urease and iron hydroxide and the layer of zirconium phosphate.

2. The cartridge of claim 1, wherein the cartridge is configured such that spent dialysate contacts the layer of urease and iron hydroxide before the spent dialysate contacts either the layer of acid zirconium phosphate or the layer of zirconium phosphate.

3. The cartridge of claim 1, wherein the cartridge is configured such that spent dialysate contacts the layer of acid zirconium phosphate before the layer of zirconium phosphate.

4. The cartridge of claim 1, further comprising a layer of activated carbon.

5. The cartridge of claim 4, wherein the cartridge is configured with a layer of activated carbon as the final layer.

6. The cartridge of claim 4, wherein the cartridge is configured such that spent dialysate contacts the layer of activated carbon after the spent dialysate contacts the layer of urease and iron hydroxide.

7. The cartridge of claim 1, further comprising a layer of zirconium oxide.

8. The cartridge of claim 7, wherein zirconium oxide in the layer of zirconium oxide comprises zirconium oxide, zirconium hydroxide, zirconium oxide hydroxide, zirconium hydrous oxide, hydrous zirconium oxide, zirconium oxide with hydration, zirconium oxide without hydration, or combinations thereof.

9. The cartridge of claim 7, wherein the cartridge is configured such that spent dialysate contacts the layer of zirconium oxide after the spent dialysate contacts the layer of acid zirconium phosphate.

10. The cartridge of claim 7, wherein the cartridge is configured such that spent dialysate contacts the layer of zirconium oxide after the spent dialysate contacts the layer of zirconium phosphate.

11. The cartridge of claim 1, wherein the layer of zirconium phosphate comprises sodium zirconium phosphate.

12. The cartridge of claim 1, wherein urease in the layer of urease and iron hydroxide is immobilized.

13. The cartridge of claim 12, wherein in the layer of urease and iron hydroxide, the immobilized urease is covalently bound to silica.

14. The cartridge of claim 1, further comprising an additional layer of zirconium phosphate.

* * * * *